United States Patent [19]

Hunt et al.

[11] Patent Number: 5,437,646

[45] Date of Patent: Aug. 1, 1995

[54] CANNULA REDUCER

[75] Inventors: Robert B. Hunt, Dover; Robert W. Schaefer, Bolton, both of Mass.

[73] Assignee: Apple Medical Corporation, Bolton, Mass.

[21] Appl. No.: 68,252

[22] Filed: May 27, 1993

Related U.S. Application Data

[63] Continuation-in-part of Ser. No. 776,194, May 15, 1991, Pat. No. 5,273,545.

[51] Int. Cl.6 ............................................. A61M 5/178
[52] U.S. Cl. ..................................... 604/167; 604/256; 251/149.1; 137/849
[58] Field of Search ............... 604/164, 165, 167, 174, 604/175, 239, 264, 272, 273, 274, 256, 249, 245-247; 606/108, 185; 128/DIG. 26, 747; 251/149.1; 137/230, 846, 849; 215/317, 224, 296; 220/212.5, 306

[56] References Cited

U.S. PATENT DOCUMENTS

| | | |
|---|---|---|
| 2,218,308 | 10/1940 | Comer ................................ 215/317 |
| 2,438,457 | 3/1948 | Schlosser . |
| 2,743,119 | 4/1956 | Covert et al. . |
| 2,766,082 | 10/1956 | Ritchey . |
| 3,097,646 | 7/1963 | Scislowwicz . |
| 3,127,894 | 4/1964 | Smith . |
| 3,313,299 | 4/1967 | Spademan . |
| 3,454,006 | 7/1969 | Langdon . |
| 3,585,996 | 6/1971 | Reynolds et al. . |
| 3,587,589 | 6/1971 | Ebner ................................ 215/296 |
| 3,853,127 | 12/1974 | Spademan . |
| 3,994,287 | 11/1976 | Turp et al. . |
| 4,000,739 | 1/1977 | Stevens . |
| 4,079,738 | 3/1978 | Dunn et al. . |
| 4,177,814 | 12/1979 | Knepshield et al. . |
| 4,649,904 | 3/1987 | Krauter et al. . |
| 4,653,477 | 3/1987 | Akui et al. ........................ 604/256 |
| 4,655,725 | 4/1987 | Honkanen et al. . |
| 4,655,752 | 4/1987 | Honkanen et al. . |
| 4,809,679 | 3/1989 | Shimonaka et al. . |
| 4,895,346 | 1/1990 | Steigerwald . |
| 4,929,235 | 5/1990 | Merry et al. . |
| 5,009,643 | 4/1991 | Reich et al. . |
| 5,104,379 | 4/1992 | Nakamura et al. ................ 604/256 |

Primary Examiner—C. Fred Rosenbaum
Assistant Examiner—Ronald K. Stright, Jr.

[57] ABSTRACT

A laparoscopy cannula reducer has at its proximal end a resilient end seal carrying a resilient tri-cuspid valve; the valve is passive, yet allows sealing of a body cavity in surgical procedures to prevent fluid flow between the atmosphere and the body cavity, both when an instrument is carried within the cannula and when the cannula is not being used for passage of an instrument to the body and the reducer has handgripping portions for applying and disengaging the reducer over a laparoscopy cannula.

4 Claims, 3 Drawing Sheets

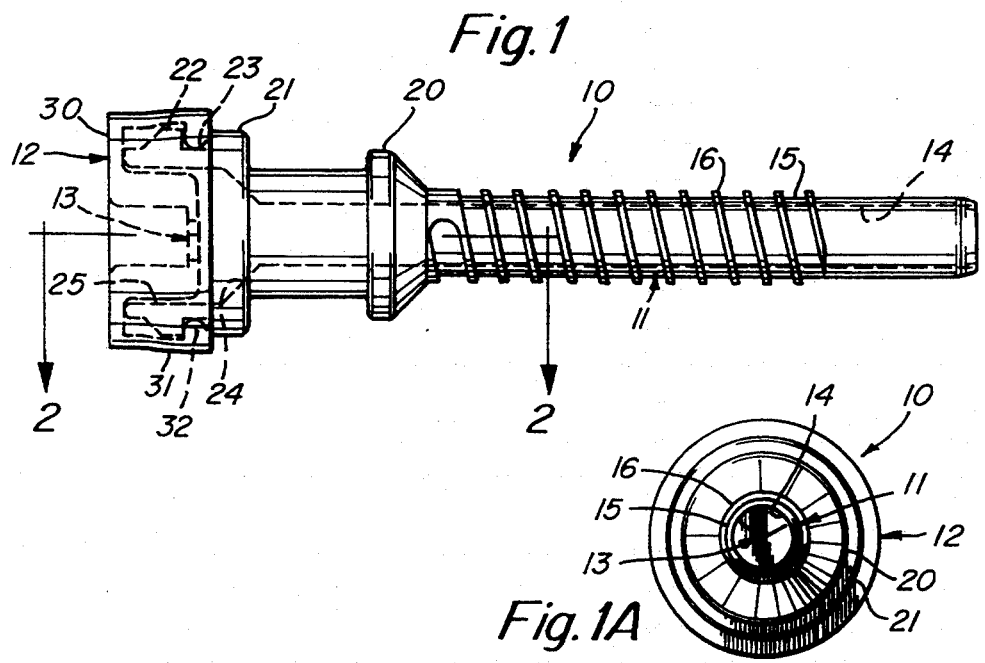
Fig. 1
Fig. 1A
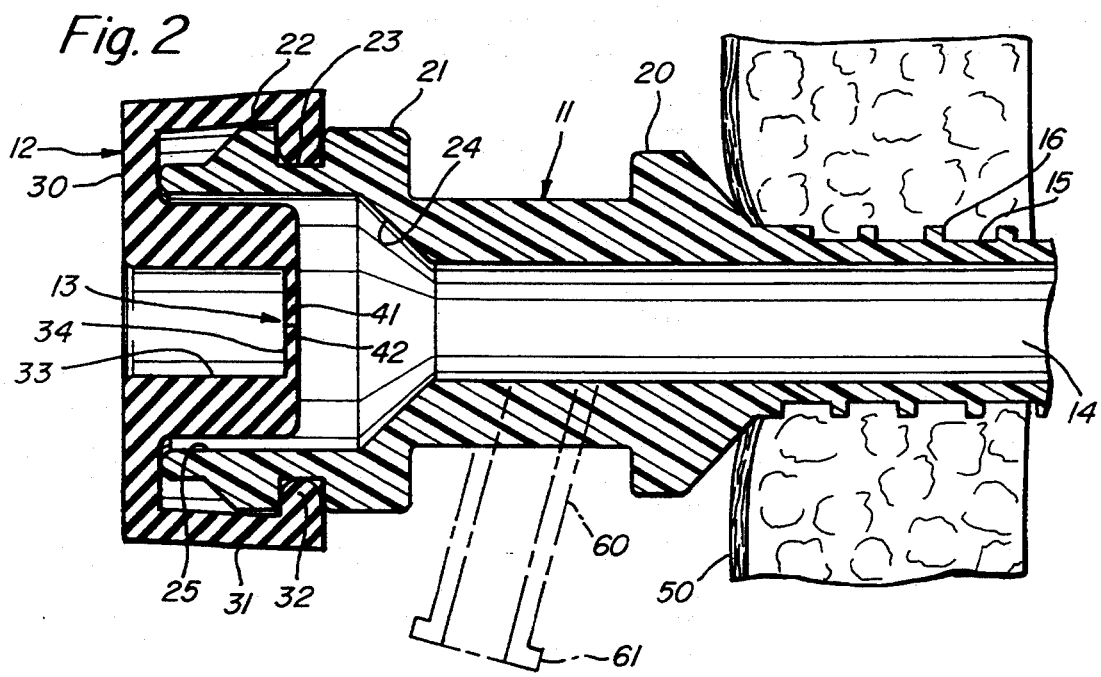
Fig. 2
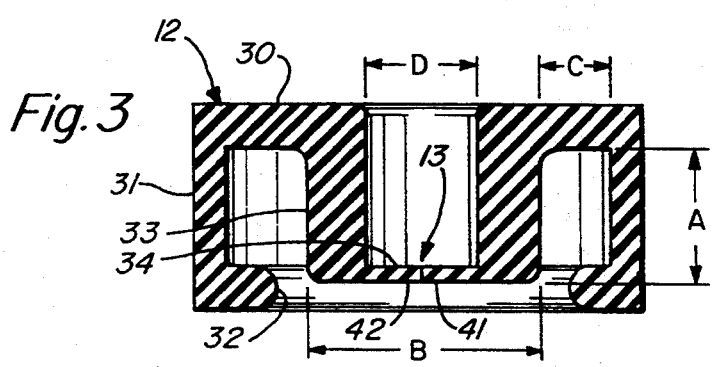
Fig. 3

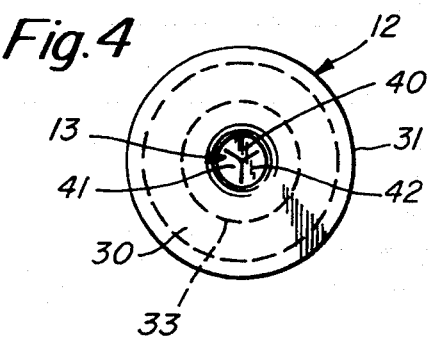
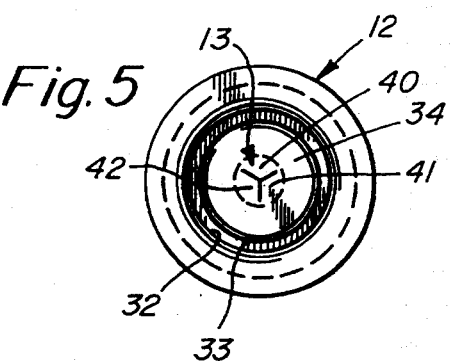
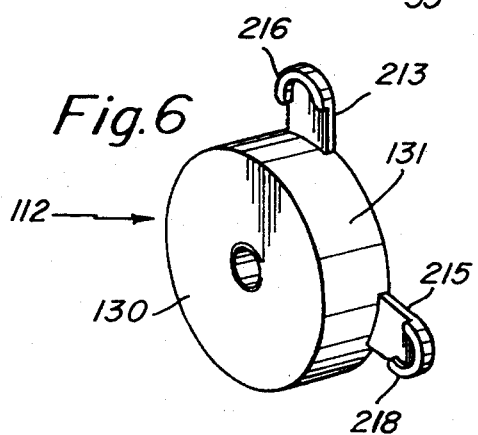
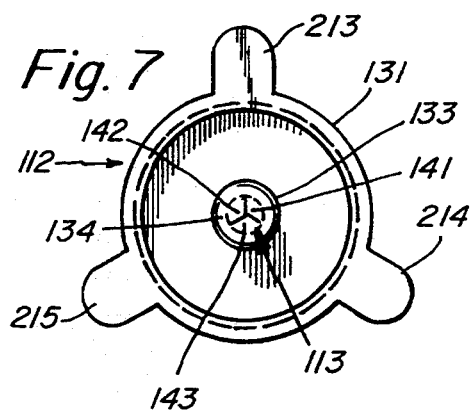
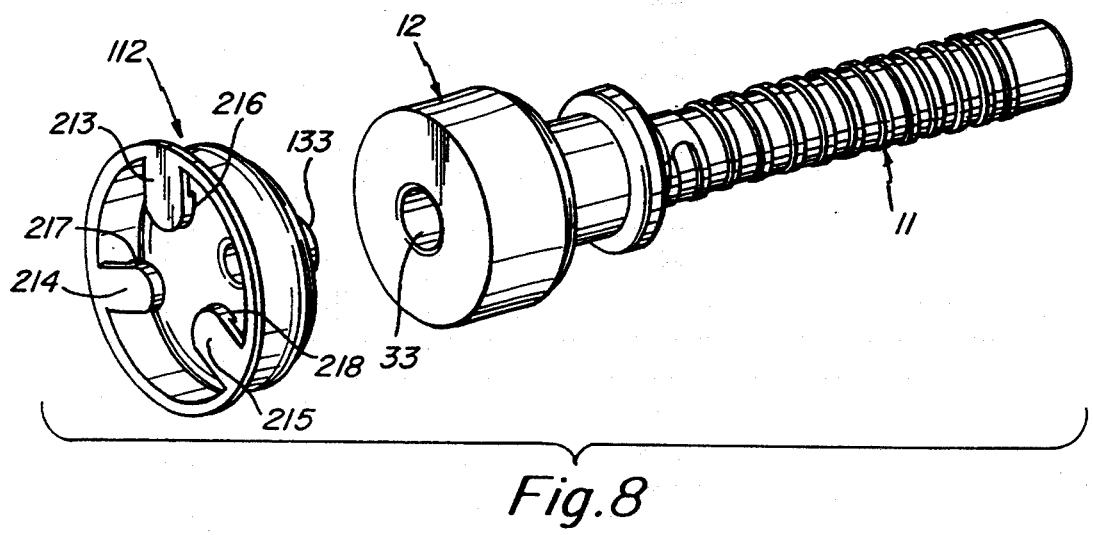

CANNULA REDUCER

RELATED APPLICATION

This application is a Continuation-in-Part of U.S. patent application Ser. No. 07/776,194, filed May 15, 1991 entitled ENDOSCOPIC CANNULA now U.S. Pat. No. 5,273,545.

FIELD OF THE INVENTION

This invention is in the field of endoscopic examination and treatment of the body of mammals, and particularly man. Medical devices are passed into the body through a body wall which, in some cases, must be sealed against fluid flow, both during use of the medical device and thereafter.

BACKGROUND OF THE INVENTION

Endoscopic procedures such as arthroscopy, hysteroscopy and laparoscopy are well known for examination and treatment of internal areas of the body. Often a seal is formed in a cannula passed through a body wall and medical devices which may be viewing or treating devices, as for example, telescopes and surgical cutting devices, respectively, can be used by passage through the seal in the body cavity. In some cases, no seal is necessary, but a seal is useful in those cases where a body fluid or gas, which may naturally occur in the body or be introduced into the body, is required to be sealed from the outside.

In laparoscopy, a medical device such as a telescope is passed through the umbilicus into a distended abdomen. This procedure is commonly used for diagnosis and therapeutic procedures. The abdomen is distended by filling the peritoneal space with carbon dioxide to separate the tissue from the organs and provide space to view the organs. Such distention of the abdomen is known as pneumoperitoneum.

The telescope placed into the abdomen is put through a cannula which can be a steel, aluminum, fiberglass or plastic tube with a seal of some sort on the proximal end to prevent loss of gas during the procedure. Very commonly, additional puncture sites are made in the abdomen to allow the passage of an assortment of tools. These secondary cannulas have an assortment of seals at their respective proximal ends to prevent the loss of gas during the procedure.

Seals available for these cannula in the past have often been rubber caps that have circular openings that work only when the instrument is in place, filling the hole or requiring the surgeon or nurse to keep their fingers over the open hole. There are some prior art devices that have both rubber caps and hinged ball valves in combination, eliminating the need for the finger approach. Sliding trumpet valves that are pushed open when an instrument is passed through and stays open because of the instrument have also been used.

More recently, disposable cannulas that have both a rubber cap seal, as well as a flapper valve, have been used as a new approach to a sliding valve allowing sliding of the instrument in use.

In all cases, in laparoscopy and other endoscopic procedures, it is important not to let the distention media such as air or $CO_2$ which has been added, escape from the abdomen or other body cavity. In other procedures where saline or other body fluids must be sealed, it is important to prevent escape of such liquids.

It is also an advantage to be able to utilize a reducer for enabling a predetermined size seal or valve in a laparoscopic cannula to be adapted for use with a smaller diameter or different cross section medical instrument than the original seal was designed for. Thus, various reducing devices have been used for valves of laparoscopic cannula.

SUMMARY OF THE INVENTION

It is an object of this invention to provide an endoscopic cannula which can be used for laparoscopic or other such procedures for allowing access to a body cavity, and which has a resilient, tri-cuspid leaf valve providing a fluid-tight seal at a predetermined area about a medical device or at the seal location, even if the device is not in place, which seal is fluid-tight, self-forming, reusable and used without adjustment.

Still another object of this invention is to provide a cannula in accordance with the preceding object which is relatively uncomplicated to construct and use in normal surgical procedures and which is capable of automatic sealing in a rapid and efficient manner, with no activation or surgical manipulation or blockage necessary to form the seals.

Still another object of this invention is to provide an integral seal and cap arrangement for mounting at the proximal end of a cannula body as previously described, which cannula body preferably carries means for ease of positive mounting in the body.

Still another object of this invention is to provide a reducer for a cannula having a seal and cap arrangement, which reducer can be used in addition to a first seal to adapt the cannula to be used with a different diameter instrument or cross section than a diameter or cross section of instrument designed to be sealed by the first seal.

SUMMARY OF THE INVENTION

According to the invention, a laparoscopic cannula allows external access to a body cavity in one mode of operation, while preventing fluid flow from the cavity at a designated area during operation of said one mode and also during a second mode of operation where the cavity is sealed without external access. The cannula preferably has a hollow tubular body defining a passageway and having an enlargement at one area thereof designed to be positioned outside of the body. The cannula carries a tri-cuspid resilient leaf valve positioned to close said passageway, yet being yieldable to allow passage therethrough of an elongated device, while sealing the designated area which surrounds the device when said device is used in the body.

In the preferred device, the leaf valve is at the proximal end of the cannula and is maintained in position by a cap integrally formed therewith of a resilient material which is mounted on the proximal end of the cannula. The cannula body has a tubular body which, preferably, has a round outer cross-section and a screw thread. The screw thread, preferably, has a square outer flanged threaded area and there is no mold parting line at the land area of the thread so as to permit the cannula to be threaded into the body after use of a trocar as is known in the art. The formation of the screw thread without mold parting lines is an improvement that enables ease of threading and use of the cannula to seal a body opening.

In the preferred embodiment, the tri-cuspid resilient leaf valve is an integral part of the end cap and acts as a single seal for an instrument or device, whether the medical device used with the cannula is in place or not. Additionally, the tri-cuspid valve acts as a gas and/or liquid seal and can act to aid in providing lateral support for an elongated instrument used during the medical procedure.

In a preferred embodiment a resilient reducer for a laparoscopy cannula valve is designed to accept and seal a first diameter elongated medical instrument therethrough. The reducer carries a collar defining an end wall carrying a tri-cuspid resilient, leaf valve positioned to produce a fluid seal to a second diameter medical instrument inserted therethrough. The reducer collar is carried by an outer wall having a resilient surrounding skirt positioned to resiliently engage and hold the tri-cuspid resilient leaf valve in position aligned with the first-mentioned laparoscopy cannula valve. The skirt carries handgripping portions for manually engaging the reducer with the laparoscopy cannula valve to provide a seal for a second diameter elongated medical instrument. The collar defines a central elongated axis and further defines a substantially planar end wall substantially perpendicular to the axis which carries the tri-cuspid leaf valve.

It is a feature of the reducer that it can be snapped into place easily to reduce the size of pre-existing valves in a wide variety of cannula configurations and valves. The reducer seals smaller diameter medical instruments than the diameters originally provided for as by a tri-cuspid valve of a laparoscopy cannula by forming a tri-cuspid seal for the device. The outer edges of the reducer are sealed because of the resiliency of the reducer causing the reducer to seal with an underlying surface such as the surface of an underlying end cap carrying a tri-cuspid valve in accordance with the preferred embodiment of the laparoscopic cannula in accordance with this invention.

It is a feature of this invention that because a single seal is used in a cap or in the reducer of this invention, a surgeon no longer has to be concerned with blocking the passageway when no instrument is in the cannula, nor does he have to park an instrument in the cannula during the procedure to avoid use of his finger to seal the cannula. A single hand can be used in some procedures. The re-entrant profile of the cap or reducer can provide a lower profile close to the body which can reduce bulk, clutter and enable desired manipulation of the medical device. The cannula of this invention is formed of a single integral cap carrying the seal which has no separable parts, eliminating the possibility of breaking of the valve and leaving of parts inside of a patient. Since there are no mechanical moving parts, but simply tri-cuspid resilient leaves of soft design, instruments are not damaged when passing through the device and can pass therethrough substantially unimpeded with slight pressure application. Objects such as tools, sutures, needles, electrocautery and telescopic devices can provide lateral support for the instruments in use. An air-tight seal is accomplished in both modes of operation of the device and if desired materials are used, low friction surfaces can be presented to medical devices passing through the seal. The seal allows tying of sutures external to the body and passing the sutures and knots through the cannula to be positioned in the abdomen without the loss of pneumoperitoneum. The seal is a passive seal in that no adjustment or manipulation is necessary.

BRIEF DESCRIPTION OF THE DRAWINGS

The above and other object, features and advantages of the present invention will be better understood from a reading of the following specification in conjunction with the accompanying drawings in which:

FIG. 1 is a side plan view of an endoscopic cannula in accordance with the preferred embodiment of this invention;

FIG. 1A is a right end view thereof;

FIG. 2 is a cross-sectional view through a proximal end thereof at line 2—2 thereof;

FIG. 3 is a cross-sectional view through a valve cap thereof;

FIG. 4 is a top plan view of the cap of FIG. 3;

FIG. 5 is a bottom plan view thereof;

FIG. 6 is a front perspective view of a preferred embodiment of a reducer for use in connection with a cannula such as the cannula of the preferred embodiment of this invention;

FIG. 7 is a rear view thereof;

FIG. 8 is an exploded perspective of the reducer of FIG. 6 ready for mounting on a laparoscopy cannula in accordance with this invention;

DESCRIPTION OF PREFERRED EMBODIMENTS

Figure 9:
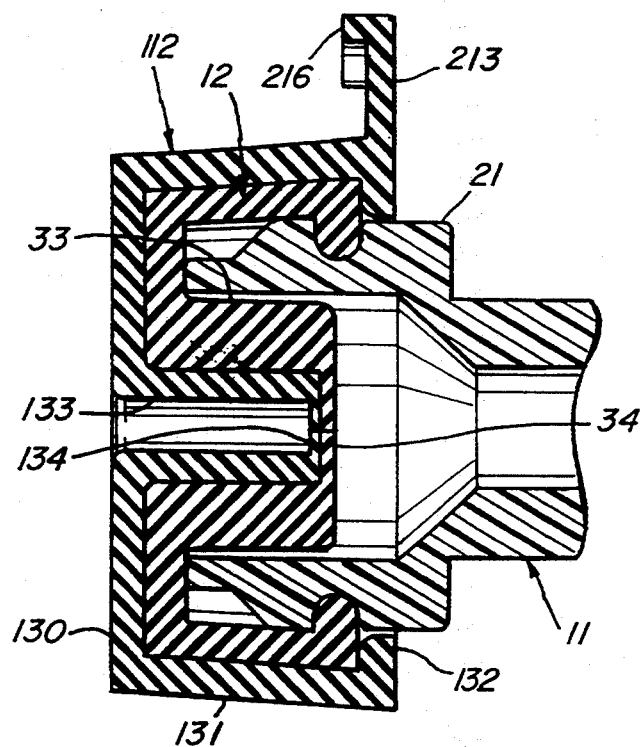
FIG. 9 is a longitudinal cross-sectional view through the central axis of the reducer of FIG. 7 in place on the laparoscopy cannula of FIG. 1.

A laparoscopy cannula in accordance with the preferred embodiment of this invention is shown in FIG. 1 at 10 and comprises a hollow, tubular body 11 and an end cap 12 at a proximal end thereof. The end cap carries a resilient, tri-cuspid leaf valve illustrated generally at 13.

The tubular body 11 is elongated, generally cylindrical and axially extended about an axially extending cylindrical passageway 14. The cylindrical outer surface 15 of the tubular body provides a land surface for a helical thread 16, preferably having a square cross-section as best shown in FIG. 1. The shank of the body which forms the outer surface 15 is free of mold parting lines. Thus, as will be described, the tubular body can be screwed through a body wall without parting lines on the land or shank portion 15, creating a stop or irritation to the body as the cannula is screwed into the body. At the proximal end of the cannula, is a first circular flange 20 lying in a plane perpendicular to the central axis of central passageway 14 acting as a stop and gripping member, a second concentric circular flange 21 and a third concentric flange 22 providing an indentation 23 for mounting of the end cap of this invention as will be described.

The tubular body 11 defines the cylindrical passageway 14 which is flared at its proximal end, as indicated at 24, to a wider diameter circular bore 25, to allow entrance of re-entrant end cap 12. The body 11 is preferably formed of a hard plastic material such as Delrin, a trademarked product of DuPont DuNemours of Wilmington, Del., which is resistant to burning by lasers and the like. Other plastics or metals can be used if desired, as for example, stainless steel, polypropylene, nylon, silicone rubber, siloxanes and the like. Preferably, the body 11 is rigid in all conditions of use, but in some cases can be somewhat resilient or pliable.

In the preferred embodiment, the tubular body 11 has an overall length of 3.260" to 3.270" and preferably 3.265"; an outside diameter at the distal end of 0.260" to 0.270" and preferably 0.265"; with a raised screw thread diameter of 0.310" to 0.320" and preferably 0.315". The screw pitch is eight threads per inch. The passageway 14, preferably has a proximal end diameter at 25 of from 0.490" to 0.510" and in the preferred embodiment, 0.500", with a distal end diameter of 0.227" to 0.233" and preferably 0.230".

The body can be opaque or colorless as desired. Preferably, the body is radioluscent. It is preferably made in a single piece, molded and unscrewed from the mold after forming, in order to avoid a parting line which could cause a problem in screwing the cannula into the body.

The end cap 12, as best shown in FIGS. 2-5, comprises a generally cylindrical cross-section having a re-entry right angle cross-section as best shown in FIGS. 2 and 3. Preferably, the end cap is formed of a single, molded piece. Materials useful for the end cap are those that will enable formation of an integral valve and include resilient materials such as NPC 940 commercial grade silicone rubber available from Dow Chemical Company of Midland, Mich. Such material can have a tensile strength of 1050 psi, hardness of 41 Shore A Durometer, elongation of 500% as measured by ASTM D412. Generally Silastic materials are preferred for use (silicone, rubber products produced by Dow-Corning of Midland, Mich.).

It is preferred that the end cap comprise a re-entrant cross-section, as best shown in FIG. 2. Thus, an end wall 30 has a surrounding cylindrical skirt 31 with a locking tab 32 engaging and snugly fitting the space between flanges 21 and 22 of the tubular body. A re-entrant, cylindrical portion 33 has a distal end wall 34 which carries the re-entrant seal.

As best shown in FIGS. 4 and 5, the re-entrant seal is formed by a tri-cuspid, resilient, leaf valve 13 having tabs 40, 41 and 42. These tabs are designed to provide a gas seal at pressure differentials of from 0 to 20 mm Hg. between the body and the atmosphere when in the position shown in FIG. 4. The seal is enhanced by the thickness of the material at the distal end wall 34, which is preferably 1/32" and preferably from 0.030" to 0.040". The seal can be maintained when a medical device such as an elongated surgical device, telescope or the like is inserted through the seal. When a medical device is inserted through the seal, the seal which is originally flat, as best shown in FIG. 2, or can be slightly cone-shaped, is pushed inwardly to expand, yet still maintain a gas and liquid seal between the instrument and the members 40, 41, 42. Thus, the device can be pushed through the seal, manipulated in the body around the end wall of the seal. The cone and enlarged cylinder end of the tubular body can aid in supporting the device for manipulation while maintaining the seal. Withdrawal of the tubular device through the seal leaves the seal intact, both in the passive position shown and the active position when a device is therein.

The tri-cuspid valve has at least three, preferably equal sized, leaves 40, 41 and 42, but can have more in some cases. For example, four and five or more leave valves having four or five radial slits can be used, so long as the seal remains self-sealing and can seal about a generally cylindrical instrument. All such valves are included in the term "tri-cuspid valve." Preferably, the slits forming the leaves of such valve define radii of from about 0.0625 inch to 0.120 inch and in the preferred embodiment of 0.08 inch and are 120 degrees apart.

Because the tri-cuspid valve is integral with the cap, good contact with the tubular body 11 can be maintained with only a single seal necessary in both modes of use of the device. The unitary nature of the seal and end cap also aids in reducing cost and increasing ease of manufacture, as by molding of a single end cap and cutting of the tri-cuspid tabs of the end seal. The end seal at the tri-cuspid valves can be cut, as known in the art. Preferably the end wall has a thickness of from 0.030" to 0.040". This may vary somewhat, depending upon the specific elastomeric material of the end seal.

Other useful elastomeric materials include but are not limited to nylon, polypropylene, polyethylene, polyesters, polyurethanes and other film forming materials, including synthetic organic polymers and copolymerized materials In the preferred embodiment, the end cap is re-entrant, that is, the cylindrical wall portion 33 is provided to pass within the tubular body while the outside flange 31, along with circular locking tab 32, mount the seal on the proximal end. Preferably, the re-entrant distance A is from 0.245" to 0.260", the diameter B is from 0.432" to 0.442", the spacing C is from 0.155" to 0.165", diameter D is from 0.212 to 0.218", with the wall thickness of wall 30 being from 0.059" to 0.066", wall 33 from 0.107" to 0.115", wall 31 from 0.041" to 0.051". Because the wall thickness of wall 33 is preferably maintained greater than the wall thickness of the seal at end wall 34, it is believed that only the end wall 34 allows flexing of the tri-cuspid valve flaps without unwanted bending of other portions of the seal when a device is inserted through the seal and manipulated at angles to its axis. In the preferred embodiment A=0.250", B=0.437", C=0.160", D=0.215", wall thickness of 30 is 0.062", 33 is 0.111", 31 is 0.046" and wall 34 is 1/32".

In use of the cannula of this invention, the cannula is positioned outside the body and a trocar, i.e. a metal, pointed piercing tip, is passed through the cannula out the righthand end as shown in FIG. 2. The peritoneal wall is then pierced by the piercing tip and the tubular body screw threaded into the wall as the piercing tip is withdrawn. The seal 13 prevents exchange of fluids or gases between the body and the atmosphere. The cannula body seals itself around the outside of the tubular portion 11 as the body tissue which has been stretched, compresses about the cannula. Often in a next step when laparoscopic procedures are being performed, carbon dioxide gas can be pumped through another cannula positioned in the body to extend a cavity within the body and allow viewing. In another step, a viewing device such as a telescope is passed through the seal 13 and into the body cavity. Note that the body wall is shown generally at 50 in FIG. 2. After use, the device is simply unscrewed and removed from the body.

At no time does the surgeon performing the operation have to be concerned with sealing the body with his finger or with any external device. The single passive seal provides good sealing. The seal is preferably effective at pressure differentials such as normally encountered in the body and after pumping of a distending gas such as carbon dioxide into the cavity. While laparoscopic procedures have been described, other endoscopic procedures such as hysteroscopy and arthroscopy, where fluids are to be sealed, can be carried out using the cannula of this invention.

In some embodiments of the invention, additional radial entrance passageways can be used to provide additional access to the body. For example, as suggested in dotted outline at 60, 61 of FIG. 1, a side tube 60 can be formed with a Luer lock end 61. This passage is ordinarily sealed by a stopper which can be removed to access the body if desired.

With reference now to FIGS. 6–11, a reducer in the form of an end cap 112 is illustrated for use with the laparoscopy cannula to act to enable a second cross section or diameter elongated medical device, having a cross section or diameter smaller than the medical device for which the end cap 12 is designed, to be used with a laparoscopy cannula of this invention. The reducer 112 can also be used to enable small diameter or different cross section devices to be used with other laparoscopy cannula having end seals designed for use with larger diameter or cross section, elongated medical devices such as catheters or the like, In FIGS. 6–11, corresponding structures to those found in FIGS. 1–5 are noted with the same number and in the case of the end cap or reducer 112, the corresponding numbered and corresponding structures to that shown in FIGS. 1–5 are noted with the number 100 added to the number shown in FIGS. 1–5. Thus, the reducer is noted at 112. All structures of the reducer 112 are as shown and described with respect to FIGS. 1–5 except that they are sized somewhat differently when used so as to provide a reducer action, i.e., the tri-cuspid valve 113 forms a better seal with a smaller diameter elongated medical instrument than does the size of the tri-cuspid valve 13 because of the specific dimensioning of the flaps such as 141, 142 and 143.

Thus as previously described with respect to end cap 12, the reducer 112 has a resilient, tri-cuspid leaf valve 113 corresponding to valve 13. The reducer is preferably formed of a single molded piece of material as previously described with respect to end cap 112. End wall 130 acts to carry the encircling cylindrical portion or enclosing collar 133 corresponding to collar 33 of FIG. 5.

The only difference between the reducer 112 and the original end cap 12 is the sizing of the tri-cuspid seal and perhaps other components, if desired, and the use of preferably integral hand gripping portions or tabs 213,214 and 215, The taps 213, 214 and 215 can be any extensions from the cylindrical skirt 131 which enable a user to invert and/or manipulate the reducer so as to easily mount it on a laparoscopy cannula such as the device 10 of FIG. 1.

As best shown in FIG. 8, the reducer 112 is inverted into a nipple like form with the reentrant cylindrical portion 133 extending outwardly to be inserted into the corresponding cylindrical portion 33 of end cap 12. The parts of FIG. 8 are brought together into mating engagement and the end cap 112 is again inverted into the form shown by the cross section of FIG. 9 where the second tri-cuspid resilient leaf valve carried by end wall 134 of the re-entrant cylindrical collar is preferably aligned and substantially adjacent to the tri-cuspid valve of the end cap 12.

Because the manual or handgripping portions are present, these elements 213,214 and 215 enable ease of mounting of the reducer and removal of the reducer by a hand action. Although tabs are shown in FIG. 6 for the preferred end cap 112, which tabs preferably have enlarged raised U-shaped ends at 216, 217 and 18, the specific shapes of the hand grips can vary greatly. In some cases, they can be mere flat extensions, a single handgripping tab can be used, two or any plurality of tabs can be used. In all cases, a gripping portion is provided which can be flat, round, or of any cross-sectional shape to provide a pull to lift the circular skirt 131 and enable engagement or disengagement as desired with an underlying laparoscopy cannula.

While the reducer 112 is preferably used with a mating and similarly configured end cap 12, as shown in the preferred embodiment, the reducer can be used with laparoscopy cannulas of all kinds to provide a reduced diameter seal where desired. In most cases, such seal is a second seal to an already existing first seal. For example, when the original laparoscopic cannula is designed as a 12 mm seal at end cap 12, positioning of a suitably dimensioned reducer 112 thereover can enable use of a 5 mm diameter or some other smaller diameter elongated medical instrument with good sealing. Ordinarily, if there is a big difference in the diameter of the instruments used, a single seal size may not suffice to provide good sealing in all cases, as will be obvious to one skilled in the art.

The reducer 112 quickly and efficiently allows variation in use of the laparoscopy cannula of FIG. 1, or any other laparoscopic cannula having a configuration which will accept the reducer 112 with the tri-cuspid valve portion 113 properly aligned with the axis of the cannula.

Figure 10:
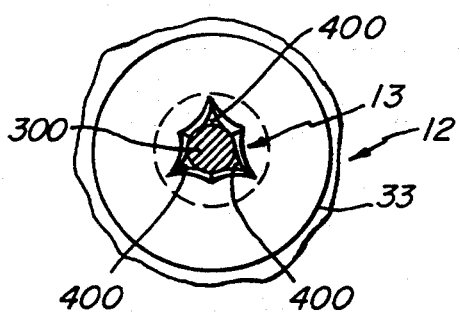
FIG. 10 is a front view of a reducer designed for a specific diameter instrument.
Figure 11:
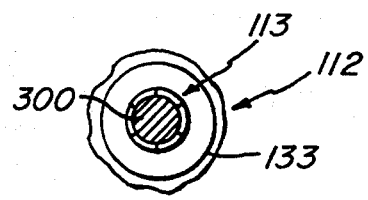
FIG. 11 is a partial rear view of a reducer nipple, for example, carrying an elongated instrument sealed therein.

FIGS. 10 and 11 show the sealing of a 5 mm elongated medical instrument 300 in a properly designed tri-cuspid seal of the reducer 112. FIG. 10, on the other hand, shows the same instrument passed through a tri-cuspid valve of an end cap 112 designed for use with a 12 mm diameter elongated medical instrument. Pressure leaks can occur at 400 where the medical instrument is too small in diameter or cross section to allow proper sealing.

The seal of FIG. 10 can be designed for 10 or 12 mm diameter medical instrument while the reducer of 112 of FIG. 11 is designed for a 5 mm medical instrument. Application of the reducer 112 of FIG. 11 over the end cap 12 of FIG. 10 as shown in the cross section of FIG. 9, provides an adaptation of a cannula to receive and seal a 5 mm diameter medical instrument, rather than the originally designed use for a 12 or 10 mm medical instrument.

As previously discussed, the reducer 112 is substantially similar to the end cap 12 with all structures being the same when numbered in the 100 series and having the handgripping tabs to allow ease of manipulation in use.

When the end cap 12 is designed to receive and seal a 12 mm instrument, its measurements would typically be A=0.200, B=0.875, C=0.184 and D=0.492 and the reducer 112 would typically have dimensions of A=0.243, B=0.875, C=0.188 and D=0.498.

While it is preferred that the end walls 134 and 34 of the reducer 112 and end cap 12 be touching, they can be spaced from each other if desired. The reducing action occurs whenever the tri-cuspid seal dimensions are smaller in the reducer 112 than the end cap 12 or other seal to be reduced.

It is a feature of this invention that the design requires no personal manipulation and is a passive seal in that it acts to seal at all times without activation. The seal allows passage of axially extending medical devices of all type, along with sutures if required. It is another feature that the tri-cuspid valve of this invention can seal a variety of different diameter medical instruments passed therethrough. For example, when the passageway 11 is 5.7 millimeters, the tri-cuspid valve can seal instruments having diameters of from 1.2 to about 5 mm. Because there is only a small pressure required to insert or withdraw the medical instrument from the tri-cuspid seal and since the threads form a firm anchor in the body, such instrument can be inserted or withdrawn from the body without holding the cannula 11, thus leaving the practitioner's hands free for other use. The reducers of this invention are useful when large variations are used in medical device diameters to be sealed by cannula seals such as seal 13.

While specific embodiments of the invention have been shown and described, it will be obvious that many variations are possible. For example, the specific length, diameter and sizing of components can vary greatly, depending upon the particular usage desired.

What is claimed is:

1. A laparoscopy cannula for allowing external access to an individual's body cavity in one mode where a first cross section elongated medical device is positioned therein, while preventing fluid flow from said cavity at a designated area in said one mode, and also preventing said fluid flow during a second mode where said cavity is sealed without external access, said cannula comprising, a hollow, substantial tubular cannula body defining a passageway and having an enlargement at one area thereof designed to be positioned outside the individual's body, said tubular cannula body carrying a first tri-cuspid, resilient, leaf valve positioned to close said passageway, yet being yieldable to allow passage therethrough of said first cross section elongated medical device while being designed and dimensioned to seal said designated area which surrounds said first cross section elongated device while said device is used in the individual's body, said tubular cannula body further carrying a separate resilient reducer resiliently engaged therewith, said reducer comprising a second tri-cuspid, resilient, leaf valve carried on an end wall of a re-entrant cylindrical collar with said end wall positioned towards said first mentioned leaf valve, said cylindrical collar being mounted on an outer end wall of said reducer with a cylindrical skirt extending from said outer end wall to resiliently and releasably mount said reducer over said tubular cannula body and to axially align said first and second tri-cuspid, resilient leaf valves, said second tri-cuspid, resilient, leaf valve being designed and dimensioned to form a fluid seal with a second cross section elongated medical device different then said first cross section elongated device, said first and second cross sections having first and second diameters respectively and said second diameter being smaller than said first diameter.

2. A laparoscopy cannula in accordance with claim 1 wherein said first and second tri-cuspid valves are axially aligned and substantially adjacent each other.

3. A laparoscopy cannula in accordance with claim 2 wherein said first valve is carried on a first end wall of a re-entrant cylindrical collar mounted on said cannula body and said end wall of each of said first and second valves are substantially planar.

4. A laparoscopy cannula in accordance with claim 3 wherein said reducer can be resiliently inverted in a nipple shape to engage said first valve and then returned to an original shape mounted on said first valve.

* * * * *